United States Patent [19]
Huckins et al.

[11] Patent Number: 5,098,573
[45] Date of Patent: Mar. 24, 1992

[54] BINARY CONCENTRATION AND RECOVERY PROCESS

[75] Inventors: James N. Huckins; Jon A. Lebo, both of Columbia, Mo.; Mark W. Tubergen, Lindenhurst, Ill.; Gamini K. Manuweera; Virginia L. Gibson, both of Columbia, Mo.; Jimmie D. Perry, Fort Collins, Colo.

[73] Assignee: The United States of America as represented by the Secretary of the Interior, Washington, D.C.

[21] Appl. No.: 730,014

[22] Filed: Jul. 12, 1991

Related U.S. Application Data

[63] Continuation of Ser. No. 581,628, Sep. 12, 1990, abandoned.

[51] Int. Cl.$^5$ ............................................. B01D 61/24
[52] U.S. Cl. .................................... 210/644; 210/649
[58] Field of Search ...................... 210/321.6, 634, 635, 210/638, 643, 644, 645, 648, 649-654

[56] References Cited

U.S. PATENT DOCUMENTS

| | | |
|---|---|---|
| 3,339,341 | 9/1967 | Maxwell et al. |
| 3,463,728 | 8/1969 | Kolobow et al. |
| 3,567,632 | 3/1971 | Richter et al. |
| 3,951,789 | 4/1976 | Lee et al. |
| 3,956,112 | 5/1976 | Lee et al. |

OTHER PUBLICATIONS

Mehrle, "Research Pre-Proposal", Mar. 1989.
Huckins, "A Novel approach for Monitoring and Subsequent Cleanup of Non-polar Contaiminants in Water," p. 96.
Miscellaneous Materials.
Chiou, "Partition Coefficients of Organic Compounds in Lipid-Water Systems & Correlations with Fish Bioconcentration Factors", 1985, pp. 57-62.
Lebo, "Personal Data Log", 1988.
Huckins, "Overview of the Development of Potential Application of Semi Permeable Polymeric Films in Enviromental Analytical Science".
Hassett et al., "A Passive In-Situ Sampler for Organic Compounds in Water", Sep. 1989, pp. 496-501.
Roff et al., "Handbook of Common Polymers", misc. pages.
Sodergren, "Solvent-Filled Dialysis Membranes Simulate Uptake of Pollutants by Aquatic Organisms", 1987 pp. 855-859.
Stalling et al., "Clean up of Pesticide and Polychlorinated Biphenyl Residues in Fish Extracts by Gel Permeation Chromatography", 1972.
Huckins et al., "A New Approach for the Cleanup of Organic Contaminants" Version 1, Oct. 1989 pp, 1-15.
Huckins et al., "A New Approach for the Cleanup of Organic Contaminants", version 2, 1989 pp. 1-17.
Huckins et al., "Semipermeable Membrane Devices Containing Model Lipid: A New Approach . . . ", Jan. 1990, 1-24.
S-Cubed, "Permeable & Microporous Membranes for Water Sampling: A Literature Review", pp. 1-33.
Tindle et al., "Apparatus for Automated Gel Permeation Clean up for Pesticide Residue Analysis", 1972, pp. 1768-1773.
Huckins et al., "Polymeric Film Dialysis in Organic Solvent Media for Clean up of Organic Contaminants", 1990 pp. 290-293.
Unknown, "Flow in Non porous Membranes", pp. 67-78.
Lieb et al., "Biological Membranes Behave as Nonporous Polymeric Sheets with Respect to the Diffusion of Non-Electrolyes", Oct. 1969, pp. 240-243.

*Primary Examiner*—Frank Sever
*Attorney, Agent, or Firm*—E. Philip Koltos

[57] ABSTRACT

A binary process for the concentration and recovery of contaminants from an aqueous environment by submerging lipids (11) inside of a thin non-porous polymeric film enclosure (10) in an aqueous environment (13) to concentrate the contaminants in the lipids (11) and polymeric film (10); and, recovering contaminants or impurities from the first part or from other contaiminated lipids or biogenic extracts by sumberging the polymeric film enclosed materials (10) in a solvent medium (16).

6 Claims, 1 Drawing Sheet

BINARY CONCENTRATION AND RECOVERY PROCESS

This application is a continuation of application Ser. No. 07/581,628, filed Sept. 12, 1990.

TECHNICAL FIELD

The present invention relates to the field of membrane separations in aqueous and organic environments in general, and in particular to a binary process for concentrating aqueous organics and for separating contaminants from liquids.

BACKGROUND OF THE INVENTION

The present invention is directed to the separation of low molecular weight organic contaminants from aqueous environments such as ponds, streams, lakes, rivers, estuaries or the like, or biological extracts, into organic solvents, using substantially non-porous polymers to enclose lipids in the dialysis of such contaminants. More specifically it includes the use of non-porous polymeric films as contaminants or impurities from biogenic extracts or liquids into organic solvent.

Non-porous polymeric membranes are so-called because the can be generally considered non-porous but are known to have pseudo-pores or transport corridors in the range of 5 to 10 Å in diameter They are stable in a variety of organic solvents and biogenic extracts, and are ideal for the dialytic separation of organic contaminant residues because most toxic organic contaminants have cross-sectional diameters of less than 10 Å.

As can be seen by reference to the following U.S. Pat. Nos. 3,339,341; 3,463,728; 3,567,632; 3,951,789; and 3,956,112; the prior art is replete with myriad and diverse processes for separating a solute from a solvent and for extracting solutes via membranous diffusion.

While all of the aforementioned prior art constructions are more than adequate for the basic purpose and function for which they have been specifically designed, these constructions function poorly in the separation of low molecular weight organic contaminants from aqueous environments or the removal of contaminants from biogenic extracts into organic solvents.

Existing techniques applied to the extraction of organic contaminants from an aqueous environment directly into a low molecular weight organic solvent have been relatively unsuccessful. The low molecular weight of most organic solvents used in this context requires the use of substantially non-porous polymeric membranes to enclose these solvents in order to prevent the solvent from escaping its enclosure through the pores of the membrane. Even so, a significant amount of solvent is lost over time in dialytic or monitoring procedures, which prohibits contaminant residues in the enclosed solvent from reaching their equilibrium concentrations.

In addition, common methods of separating organic contaminants from lipids or biogenic extracts are often inadequate for removing significant but low concentrations of the contaminants from lipids or biogenic extracts. These methods include destructive acid or base hydrolysis, adsorptive chromatography, gel permeation or size exclusion chromatography and liquid-liquid partitioning. A major drawback of these methods is the large solvent requirement for the chromatographic techniques and their relatively low lipid capacity, as well as the failure of liquid-liquid partitioning to prevent large neutral lipids from carrying over to the non-polar liquid phase with the contaminants of interest.

As a consequence of the foregoing situation, there has existed a long-standing need for a process or processes that can accomplish the of low molecular weight organic contaminants or impurities from aqueous environments or biological extracts into organic solvent. The provision of such a construction is a stated objective of the present invention.

SUMMARY OF THE INVENTION

The present invention contemplates a novel process for the separation of low molecular weight organic contaminants from aqueous environments into lipids, and the use of substantially non-porous polymers to enclose lipids in the process. Also, the present invention provides for the efficient removal of contaminant or impurities from lipids or biogenics into an organic solvent.

In the first part of the process, an organic contaminant (or contaminants) diffuses from an aqueous environment across a non-porous polymeric membrane into a biogenic extract, lipid or lipid-like material which mimics the way fish concentrate organic contaminants from water. The second part of the process comprises the diffusion of a contaminant (s) from a lipid or biogenic extract across a semi-permeable non-porous polymeric membrane into an organic solvent.

It is a primary object of the invention to provide a simple, efficient and economic process for the concentration of organic contaminants from an aqueous environment into a lipid and then into an organic solvent, This can be optimized for use as an analytical tool to measure contaminant concentrations in the environment.

It is another and more specific object to provide a process employing a hollow construction of non-porous polymeric film such as a bag, capillary tubing or layflat tubing. or the like to enclose lipid or lipid-like materials in dialytic processes of concentrating organic contaminants.

A further primary object is the use of non-porous polymeric films as semi-permeable membranes for the dialytic separation of contaminants from biogenic extracts, lipids, or lipid-like materials into organic solvent.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
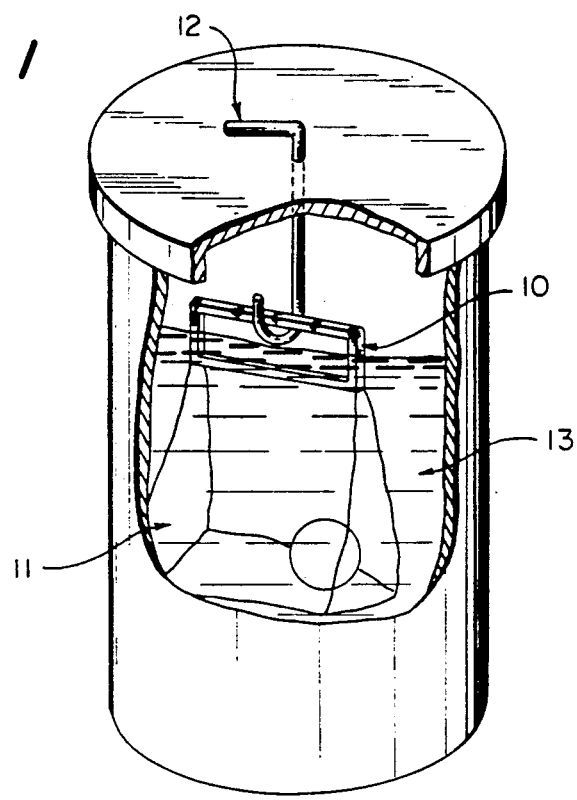
FIG. 1 is a cutaway perspective view of a typical arrangement employed in the contaminant concentration part of this invention.

Research has indicated that synthetic organic polymeric films can be used as inexpensive dialysis membranes for the separation of organic contaminants from biogenic matrices such as lipids by submerging the membrane-enclosed lipids in organic solvents. It has also been discovered that lipids, or large-molecular weight ($\geq 700$ daltons) synthetic organic compounds used as surrogate lipids, when contained in these polymeric film bags or tubes and placed in water, mimic the great concentrating power of living aquatic organisms in their passive uptake of organic contaminants from water. This aspect of the binary process results in high concentrations of contaminants in the polymer film and enclosed model lipids when compared to extremely low contaminant residues in the ambient water. This application of the invention can be used as an analytical tool for environmental contaminant monitoring and for actual pollution abatement and remediation such as cleaning up potentially harmful organic contaminants in the aquatic environment.

Testing has indicated that commercially available dialysis membranes were not stable in lipids and most organic solvents; however, polymeric films such as low density polyethylene seemed to offer an alternative because they are inexpensive, stable in a variety of organic solvents (high density polyethylene often used in solvent wash bottles), and behave like biomembranes in the diffusion of organic compounds. Although they are considered to be non-porous, these films are known to have pseudo-pores or transport corridor in the range of 5 to 10 Å in diameter. The molecules of most toxic organic contaminants have cross-sectional diameters of <10 Å. Theoretically, these characteristics appeared to be ideal for dialytic separation of organic contaminant residues from larger sized or more polar lipid molecules in organic solvents.

Another related problem facing chemists is that current methods for sampling and extracting aqueous contaminants are problematic because of handling difficulties associated with collecting and analyzing the large volumes of water often necessary to detect trace residues. Also, inability to maintain sample integrity throughout the processes of sampling, extraction and residue quantitation limits the accuracy of many techniques. These difficulties can be largely overcome by physically simulating the simple but powerful in situ residue bioconcentration process of aquatic organisms. Theory suggests that bioconcentration of organic contaminants in fish can be conceptually modeled by membrane encapsulated lipids submerged in contaminated aquatic systems. Partitioning appear to be the key elements in the process by which aquatic organisms accumulate elevated contaminant levels. Other investigators have used membrane enclosures of organic solvents as samplers of aqueous organic contaminants but observed solvent concentration factors that were at least 100 fold less than actual bioconcentration factors of the same contaminant in fish. Enclosure of model lipids in polymer film bags, capillary tubing or layflat tubing with high surface-area-to-volume ratios offers a simple physical model that would mimic the key components postulated for the bioconcentration process and would achieve the great concentrating power of lipids in aquatic organisms.

The separation aspect (organic solvent dialysis) of this binary process, relating to the removal of contaminants or impurities lipids or biogenic materials enclosed in polymeric film, has little known precedence in the literature. Methods currently known for the separation of contaminants from lipid or biogenics generally consist of destructive acid or base hydrolysis, liquid-liquid partitioning, adsorptive chromatography such as Florisil, and gel permeation or size exclusion column chromatography. Since our proposed separation process is non-destructive in nature, it is more closely related to size exclusion, adsorptive chromatography and partitioning. However, our film or membrane process is simpler in implementation, has greater lipid capacity than typical column chromatography and requires less solvent. Standard liquid-liquid partitioning, such as acetonitrile/hexane systems, do not prevent large neutral lipids from carrying over into the liquid phase with most of the contaminants of interest. This is a major advantage of our membrane-controlled size exclusion and partitioning process over the conventional approach.

Because our process uses large molecular-weight model lipids such as triolein (895.5 mw) or synthetic model lipids such as silicon fluids (>800 mw) instead of solvent, losses of these compounds to the surrounding aqueous media are prevented by membrane size exclusion. This more closely approximates the lipid containment characteristics of biomembranes in living cells and results in the full realization of theoretical lipid-water partition coefficients of contaminants. The concentration factors of contaminants in our model lipid are often similar to their Kow (octanol/$H_2O$ partition coefficient) values and to their bioconcentration factors in fish lipids at equilibrium. Both the aqueous phase and organic phase separations of this invention; i.e. removal or sampling of organic contaminants from water by model lipids enclosed in non-porous synthetic films and separation (recovery) of organic contaminants or impurities from film-enclosed lipids or other biogenics by dialysis into an organic solvent media; involve passive diffusion of contaminants (dialysis) through organic films and membrane-separated liquid-liquid partitioning. Briefly, transport rates of contaminants through the suggested polymer films (polyethylene and polyproplylene) for both aspects of this binary process control the time (kinetics) required to reach steady state or equilibrium (maximum contaminant residues in lipid or maximum contaminant recovery from lipids) between enclosed lipids and aqueous or organic solvent phases. For dialytic separations of contaminants from membrane-enclosed lipids using non-polar organic solvents such as cyclopentane, times required for optimum contaminant removal are generally less than 48 hours, with >80% of the mass of each contaminant dialyzing into the cyclopentane. The >80% residue recovery is achieved by having at least 10 fold greater solvent volume outside the film-enclosed lipids than lipid volume inside.

Times required to reach contaminant steady state between membrane-enclosed model lipids and an aqueous matrix are considerably greater than those required in the solvent-facilitated separation process. Several weeks may be required depending on the selected process configuration and the particular application. However, the length of time required can be controlled by adjusting surface-area-to-volume ratios, temperature, and polymer-related factors affecting diffusivity. The great contaminant concentrating (partitioning) power of model lipids enclosed in polymeric membranes and placed in aqueous systems is due to the fact that many major environmental contaminants are highly lipophilic, and at the same time hydrophobic, and they therefore readily partition from aqueous phases into lipids or lipid-like phases even though most of the process must occur against a steadily increasing concentration gradient (ie. much higher levels of residues in lipids than the surrounding water) to reach equilibrium. An example of a larger scale configuration is as follows: about 40 g of animal or plant oil or fat is placed in a 3 m length of 6" wide layflat, low density polyethylene tubing having a wall thickness of 0.002 or 0.005". Then the liquid is spread down the length of the tubing. Afterwards the resulting 3 m long, high surface-area-to-volume ribbon tubing is sealed with large clamps and placed in the contaminated aqueous system. By using many of these lipid-containing enclosures, contaminated water can be exposed to large amounts of lipid having sufficient surface area for adequate removal rates of contaminants from flowing water. In the case of low or no water flow a turgid configuration, ie. fill tube with lipid, may be used, which will have greater capacity for contaminants. Necessary exposure time would depend on the time required to saturate the lipid and tubing matrix with contaminants, but should be <2 months in most cases. A number of types of non-porous synthetic polymeric films can theoretically be used for this binary process, including: polyethylene, polypropylene, Silastic, ® polyvinylchloride, chlorinated polyethylene, chlorosulphonated polyethylenes, polyimides, polyethylene-vinylacetate copolymer, etc. The data presented herein was generated using polyethylene, which is generally the polymer of choice for process applications dealing with nonpolar contaminants. Relatively thin polymeric films of 0.0002 to 0.010" (5 to 254 μm) thickness are desirable for the conduct of both aspects of this process because of the need to minimize transport times of contaminants through the polymer matrix. Membrane transport is a major factor controlling times required to reach process steady state or, in most cases, process completion.

In general, increasing film thicknesses reduces permeation rates in a linear manner (constant temperature and pressure) of non-electrolytic organic compounds through nonporous synthetic polymers A film thickness of ≦0.003" is recommended for small scale (<100 mL volume of model lipids) analytical applications of both aspects of this binary process. However, process applications such as contaminant of lipid) in organic solvent media, and the use of large volumes of fats or model lipids enclosed in films for removal of organic contaminants from aqueous systems may require the greater strength and durability of the upper range of film thickness, ie. 0.004 to 0.010". Also, for hydrocarbon polymers such as polyethylene or polypropylene, properties of low density, low crystallinity (rigid or high density commercial polyethylene generally ranges from 60 to 95% crystallinity), and low chain orientation are generally desirable because these properties maximize contaminant transport rates through film matrices, These characteristics are usually present in polyethylene films used to make commercial plastic bags.

The surface-area-(film) to-volume (lipid) ratios used for film-enclosed model lipids can vary greatly depending on the nature of the particular process application. The range of potential surface-area-to-volume ratios is approximately <1 cm$^2$/g to 1000 cm$^2$/g lipid. The larger surface area configuration permits greater total residue flux into enclosed model lipid or into exterior organic solvent per unit of time, which reduces process completion time. Process configurations with large surface areas or surface-area-to-volume ratios (>100 cm$^2$/g lipid) are particularly useful for aqueous phase applications for which the time required to remove (>90% reduction) contaminant residues is an important factor in the convenience of the method. For some field applications, adequate rates of removal of contaminants from waters may require large numbers of the high surface area configurations. The capacity of the film-enclosed model lipid for removing a contaminant is determined by the contaminants's steady state distribution coefficient between the water and the selected lipid phase. This value can be estimated from the contaminant's Kow. For example a polychlorinated biphenyl (PCB), 2,2',5,5,'- tetrachlorobiphenyl, was determined to have $6.6 \times 10^5$ times higher concentration in polyethylene-enclosed carp lipid at steady state than the surrounding water. Assuming the water surrounding the film-enclosed lipid contained 1 μg/L of 2,2",5,5"-tetrachlorobiphenyl, then 1 kg of lipid could remove up to maximum of 0.66 gram of this PCB based on its steady state lipid-water distribution coefficient of $6.6 \times 10^5$. In theory then, $6.6 \times 10^5$ L of water containing 1 μg/L of PCB could be purified by 1 L of similar lipid enclosed in polyethylene film. Lower surface-area-to-volume configurations (<100 cm$^2$/g lipid) should generally be more applicable to static aqueous systems and for organic solvent dialysis (lipid-contaminant separations).

Organic contaminants or impurities in both plant and animal lipid extracts may be removed by dialyzing the film-enclosed materials in an organic solvent media. The efficiency of these dialytic separations depend on the size and polarity the contaminant molecules as well as the size and polarity of the contaminated lipid. Triglycerides often represent the largest portion of animal fat and fish oils. Because of the large molecular weight of triglycerides (generally >600 daltons), smaller, nonpolar organic contaminants or impurities (<500 daltons) are readily removed from them by using the organic solvent dialysis aspect of this invention. Both aspects of this binary process are applicable to a wide range of nonelectrolytic organic contaminants. As pointed out earlier, molecular size and polarity are the major contaminant-related factors that limit transport rates of a compound through the nonpolar polymers. In aqueous phase applications (no organic solvent interacting with the polymer), mirex (546 daltons) appears to approximate the upper size limit, as its diffusion rate through polyethylene is very slow. In organic solvent media applications, slightly larger molecular weight compounds (up to ≈600 daltons) may have marginally acceptable transport rates through nonpolar polymeric films. Organic compounds below the above size limits may still have unacceptably low transport rates through nonpolar polymeric films because of polar functional groups. For example the permeability of small molecular weight organics through polyethylene (constant temperature and pressure) decreases according to functional groups as follows: halogenated hydrocarbons, hydrocarbons, ethers, esters, ketones, aldehydes, nitroderivatives, acids and alcohols. This type of resistance to mass transport or diffusion precludes the use of highly nonpolar polymers like polyethylene, polypropylene and silastic ® for applications dealing with polar phenols, alcohols, and organic acid contaminants. However, use of these polymers to enclose lipids is applicable to the separation of many nonpolar polyaromatic hydrocarbons, aliphatic hydrocarbons, organochlorines and pesticides. Ideally, synthetic polymers can be selected that have a high affinity for the contaminant chemical classes of concern without significant polymer-contaminant interaction that would severely limit permeation rates through the matrix.

Finally, the types of lipids suitable for either part of the binary process are an important consideration in establishing the range of operating conditions of this invention. The organic solvent dialytic separation aspect of this invention is amenable to organic extracts of any plant, animal or food. The choices of model lipid for use in aqueous phase applications depend on the chemical structure of contaminants of concern. Neutral fats such as triglycerides are the model lipid of choice for concentrating non-polar contaminants such as PAHs, PCBs, dioxins, furans and some pesticides. Triolein is an excellent model for biogenic triglyceride mixtures, because it is a major lipid in aquatic organisms, and it has a low melting point and high molecular weight. Although not essential, model lipids should be liquids within the range of aqueous matrix temperatures, due to much slower transport in solid phases. Mixed triglycerides from fish oil, peanut oil, soybean oil, etc., are also acceptable models. The addition of an antioxidant may also be necessary for some extended applications because lipids that are liquids at $\leq 30°$ C. are somewhat unstable due to the potential for oxidation at unsaturated sites on the esterified fatty acid molecules. Also, many synthetic large molecular weight hydrocarbons or silicones may serve as acceptable surrogate lipids for concentrating nonpolar, aqueous organic contaminants. For more polar contaminants such as certain herbicides, organophosphate insecticides, mycotoxins, and industrial chemicals, the use of more polar membrane-associated model lipids may be necessary for optimimum aqueous recovery of these contaminants. A suitable model for more polar membrane lipids is lecithin, a common large molecular weight phospholipid. Obviously many large molecular weight synthetic, organic compounds may also serve as more polar model lipids.

The use of polyethylene or polyproplyene and several other non-porous synthetic polymeric films as semi membranes for dialytic separations of contaminants or impurities from lipids existing methods: 1) ease of implementation, requiring no costly hardware such as automated gel permeation chromatographs; 2) stability of these films in a variety of organic solvents, unlike most dialysis or ultrafiltration membranes; 3) amenability to scaling up or down for cleanup of a wide range of sample masses; 4) marked reduction in the amount of solvent required for lipid cleanup, e.g., 5 g fish oil can be processed with 200 to 500 mL cyclopentane ($C_5H_{10}$), whereas the same amount of oil would require 3 L of mobile phase (solvent) if size exclusion chromatography were used; 5) adjustability of times-to-equilibrium or completion of separations by the manipulation of surface-area-to-volume ratios and film thicknesses; 6) flexibility that will allow analysts to use reactive, adsorptive, and other chromatographic methods in sequence without interim evaporative steps, because dialysis can be accomplished using non-polar hydrocarbon solvents such as cyclopentane; and 7) amenability to automation. Enclosures of model lipids or lipid from extracts of aquatic organisms in polymeric films constitutes a more realistic physical model of the process by which organisms concentrate aqueous organic residues. It is known that the equilibrium partition coefficients of a number of organics including 2,2',5,5'-tetrachlorobiphenyl were similar in triolein-water and octanol-water systems. Therefore, contaminant Kow's should be predictive of steady state values between water and the film-enclosed lipids which is not the case for solvent filled bags. Also, film-enclosed lipid concentration factors appear to be about 200 to 2000-fold higher than values for film-enclosed solvents.

Although the diffusion of some non-electrolytic organic compounds though synthetic, non-porous polymers was known to be similar to their diffusion through biomembranes, no one has used these polymers to enclose lipids, thus physically simulating the key components of the powerful aqueous biouptake process and resulting in high concentrations of contaminants in model lipids. In theory, the diffusion of aqueous contaminants through non-porous polymeric films into enclosed lipids is largely reversible upon replacing the exterior water phase with a nonpolar organic solvent phase having an affinity for the organic contaminants. The use of non-porous polymeric films as semipermeable for the dialytic separation of contaminants or impurities from biogenic extracts into organic solvent is new. The only known separations that are comparable are those largely used in the petroleum industry in place of distillation. However these membrane-based methods have never been applied to separating contaminants from lipids or other biogenics.

Figure 2:
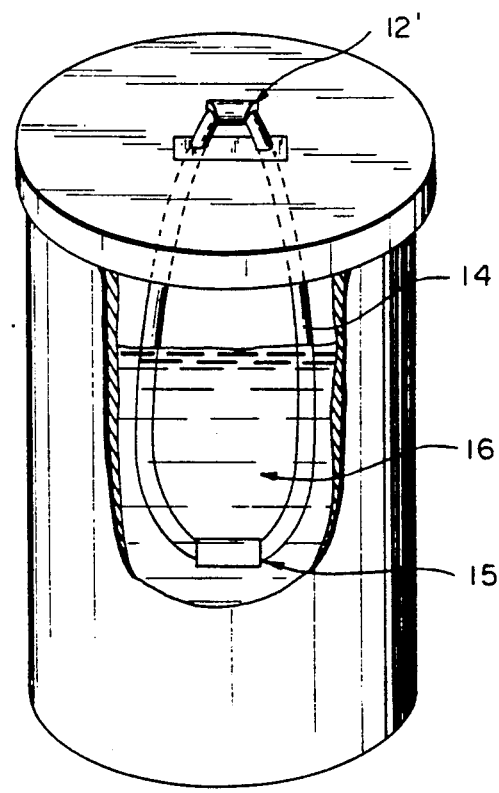
FIG. 2 is a cutaway perspective view of a typical arrangement employed in the solvent dialysis part of this invention.

Examples of laboratory test equipment used to practice the teachings of this invention are depicted in FIGS. 1 and 2. As shown in FIG. 1 a typical contaminant concentration process is depicted wherein a thin walled synthetic polymeric tubing (14) such a layflat polyethylene tubing containing lipids (15) is suspended by suitable suspension means (12) in a aqueous environment (16).

the containment recovery process is depicted in FIG. 2 wherein a weighted envelope (10) fabricated from synthetic organic polymeric films and containing contaminated lipids (11) is suspended by suitable suspension means (12) in a solvent bath (13).

Having thereby described the subject matter of the present invention, it should be apparent that many substitutions, modifications and variations of the invention are possible in light of the above teachings. It is therefore to be understood that the invention as taught and described herein is only to be limited to the extent of the breadth and scope of the appended claims.

We claim:

1. A binary process for concentration and recovery of contaminants from an aqueous environment comprising:
    a) filling a thin walled large surface area volume enclosure fabricated from a membrane of non-porous polymeric film with a class of weight synthetic organic compounds;
    b) suspending said enclosure in an aqueous environment containing lipophilic contaminants for a sufficient period of time to allow the lipophilic contaminants to become concentrated in the polymeric film filled with a class of materials including lipids and large molecular weight synthetic organic compounds; and,
    c) removing the contaminated enclosure from said aqueous environment.

2. The binary process as in claim 1, further comprising
    d) suspending said polymeric enclosure with lipophilic contaminants in a solvent medium to absorb a substantial percentage of the contaminants from the filled polymeric film.

3. The binary process of claim 2, wherein the nonporous polymeric film is selected from polyethylene, polypropylene, silicones, chlorinated polyethylene, chlorosulphonated polyethylenes, polyimides, and a polyethylene-vinylacetate copolymer.

4. The binary process of claim 2, wherein the lipids include neutral fats of triglycerides.

5. The binary process as in claim 1, wherein said enclosure is comprised of bags, envelopes, and tubes having high surface area to volume rations.

6. The binary process of claim 1, wherein the large molecular weight synthetic organic compounds have a molecular weight $\geq 700$ daltons.

* * * * *

UNITED STATES PATENT AND TRADEMARK OFFICE
CERTIFICATE OF CORRECTION

PATENT NO. : 5,098,573

DATED : March 24, 1992

INVENTOR(S) : James N. Huckins, Jon A. Lebo, Mark W. Turbergen, Gamini K. Manuweera, Virginia L. Gibson, Jimmie D. Petty It is certified that error appears in the above-indentified patent and that said Letters Patent is hereby corrected as shown below:

On the title page, Item [75] Inventors:

The name of one of the inventors is misspelled. Specifically, "Jimmie D. Petty," is misspelled as, "Jimmie D. Perry."

Signed and Sealed this

Third Day of August, 1993

Attest:

MICHAEL K. KIRK

Attesting Officer

Acting Commissioner of Patents and Trademarks